United States Patent
Soto et al.

(10) Patent No.: US 11,446,285 B2
(45) Date of Patent: Sep. 20, 2022

(54) METHODS FOR TREATING SYSTEMIC LUPUS ERYTHEMATOSUS

(71) Applicant: University of Southern California, Los Angeles, CA (US)

(72) Inventors: Maira Soto, Los Angeles, CA (US); Kevin J. Gaffney, Los Angeles, CA (US); Kathleen E. Rodgers, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 16/622,399

(22) PCT Filed: Jun. 7, 2018

(86) PCT No.: PCT/US2018/036400
§ 371 (c)(1),
(2) Date: Dec. 13, 2019

(87) PCT Pub. No.: WO2018/231614
PCT Pub. Date: Dec. 20, 2018

(65) Prior Publication Data
US 2020/0206211 A1    Jul. 2, 2020

Related U.S. Application Data

(60) Provisional application No. 62/520,897, filed on Jun. 16, 2017.

(51) Int. Cl.
*A61K 31/4439*    (2006.01)
*A61P 37/00*    (2006.01)
*A61K 45/06*    (2006.01)

(52) U.S. Cl.
CPC .......... *A61K 31/4439* (2013.01); *A61P 37/00* (2018.01); *A61K 45/06* (2013.01)

(58) Field of Classification Search
CPC ........................... A61K 31/4439; A61P 37/00
See application file for complete search history.

(56) References Cited

FOREIGN PATENT DOCUMENTS

| WO | 2014/145331 | | 9/2014 |
|---|---|---|---|
| WO | WO2014182688 | * | 11/2014 |
| WO | 2016/011420 | | 1/2016 |

OTHER PUBLICATIONS

The International Search Report (ISR) with Written Opinion for PCT US2018/036400 dated Nov. 15, 2018, pp. 1-18.
Gatto, Mariele et al. "Success and failure of biological treatment in systemic lupus erythematosus: A critical analysis" Journal of Autoimmunity (2016) vol. 74, pp. 94-105.
Kuhn, A. et al. "Advances in the treatment of cutaneous lupus erythematosus" Lupus (2016) vol. 25, pp. 830-837.
Radin, Massimo et al. "Immunotherapies in phase II and III trials for the treatment of systemic lupus erythematosus" Expert Opinion on Orphan Drugs (2017) vol. 5(1), pp. 55-69.

\* cited by examiner

*Primary Examiner* — Yong S. Chong
(74) *Attorney, Agent, or Firm* — McDonnell Boehnen Hulbert & Berghoff LLP

(57) ABSTRACT

Methods for treating systemic lupus erythematosus (SLE) are disclosed, based on administering to a subject with SLE an amount effective to treat the subject of a polypeptide including antiogensin 1-7 (A(1-7)), Nle3A 1-7, or a compound according to general formula.

5 Claims, 3 Drawing Sheets

Specification includes a Sequence Listing.

METHODS FOR TREATING SYSTEMIC LUPUS ERYTHEMATOSUS

CROSS REFERENCE

This application is a U.S. national phase of International Application No. PCT/US2018/036400, filed on Jun. 7, 2018, which claims priority to U.S. Provisional Application No. 62/520,897, filed Jun. 16, 2017, both of which are incorporated by reference herein in their entirety.

BACKGROUND

Systemic lupus erythematosus (SLE) has increased in incidence of disease over the last 50 years. Current treatments options are inadequate, as many SLE patients do not respond to current treatments and some suffer from severe side effects. New and more effective therapies that reduce the pathologies associated with SLE, without the current barrage of side effects, are crucial to the health and quality of life of these patients.

SUMMARY

In one aspect methods for treating a subject with systemic lupus erythematosus (SLE) are disclosed, comprising administering to the subject in need thereof an effective amount of a compound having the general formula 1 including salts thereof:

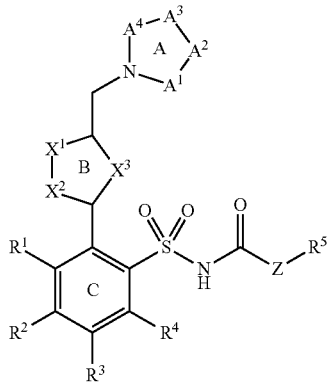

wherein:
  ring A is a five-membered or six-membered heteroaryl or heterocyclyl ring containing either a combination of two non-adjacent nitrogen or oxygen atoms, or a combination of three or four nitrogen or oxygen atoms;
  ring B is a five-membered or six-membered heteroaryl ring that contains at least one nitrogen atom;
  $A^1, A^2, A^3, A^4$ are independently selected from a group consisting of =N—, —C(=O)—, —C($R^a$)=, =C($R^b$)—, —C($R^c$)($R^d$)—N($R^e$)—, —C($R^c$)($R^d$)—O—, and —[C($R^c$)($R^d$)]$_n$—, wherein n is 1 or 2;
  $X^1$—$X^2$ is —($R^6$)C—N—, —N—C($R^6$)—, —N—N—, —N—O—, —O—N—, —N—S— or —S—N—;
  $X^3$ is —($R^7$)C=C($R^8$)—, —O—, —S—, or —N($R^9$)—;
  Z is —O—, —N(H)— or a bond to $R^5$;

$R^a$ and $R^b$ are independently selected from the group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido and carboxy,
  or $R^a$ and $R^b$ can also join to form a ring of up to 6 atoms;
  $R^c$ and $R^d$ are independently selected from a group consisting of hydrogen, alkyl, aryl, or heteroaryl, provided that $R^c$ and $R^d$, together with the atoms to which they are attached, form a ring of up to 6 atoms;
  $R^e$ is hydrogen, alkyl, aryl, heteroaryl, acyl, alkoxyacyl, aminoacyl, dialkylaminoacyl, or dialkylaminoacyl;
  $R^1, R^3, R^4, R^6, R^7$, and $R^8$ are independently selected from a group consisting of hydrogen, alkyl, alkenyl, alkynyl, aryl, heteroaryl, arylmethyl, heteroarylmethyl, fluoro, chloro, bromo, iodo, cyano, hydroxy, amino, alkylamino, alkoxy, aryloxy, alkoxyalkyl and aryloxyalkyl;
  $R^2$ is alkyl, alkenyl, alkynyl, aryl, heteroaryl, arylmethyl, heteroarylmethyl, alkoxy, trifluoromethoxy, perfluoroalkoxy, aryloxy, alkoxyalkyl, or aryloxyalkyl;
  $R^5$ is alkyl, aryl, heteroaryl, hydroxyalkyl, carboxyalkyl, alkoxyalkyl, or aryloxyalkyl; and
  $R^9$ is hydrogen, alkyl, aryl, heteroaryl, acyl, alkoxyacyl, aminoacyl, dialkylaminoacyl, or dialkylaminoacyl.

In one embodiment, ring A is selected from the group consisting of:

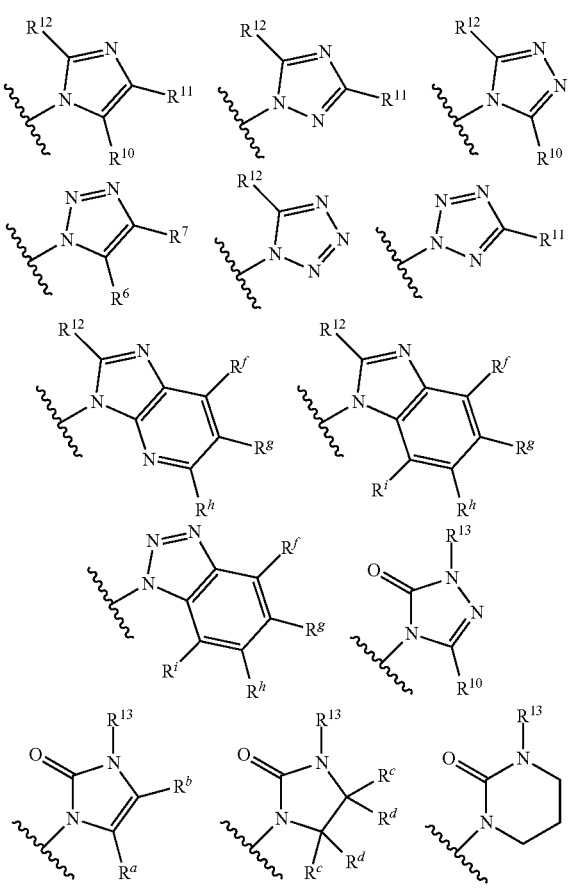

-continued

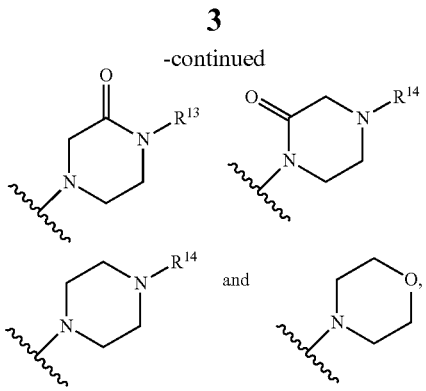

wherein:

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido and carboxy, or $R^{10}$ and $R^{11}$, together with ring A to which they are attached, form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{13}$ is hydrogen, alkyl, aryl or heteroaryl;

$R^{14}$ is hydrogen, alkyl, aryl, heteroaryl, acyl, alkoxyacyl, aminoacyl, dialkylaminoacyl, or dialkylaminoacyl; and $R^f$, $R^g$, $R^h$, and $R^i$, are independently selected from a group consisting of hydrogen, alkyl, alkenyl, alkynyl, aryl, heteroaryl, arylmethyl, heteroarylmethyl, fluoro, chloro, bromo, iodo, hydroxy, amino, alkylamino, alkoxy, aryloxy, alkoxyalkyl, or aryloxyalkyl;

or a salt thereof.

In another embodiment, ring B is selected from the group consisting of:

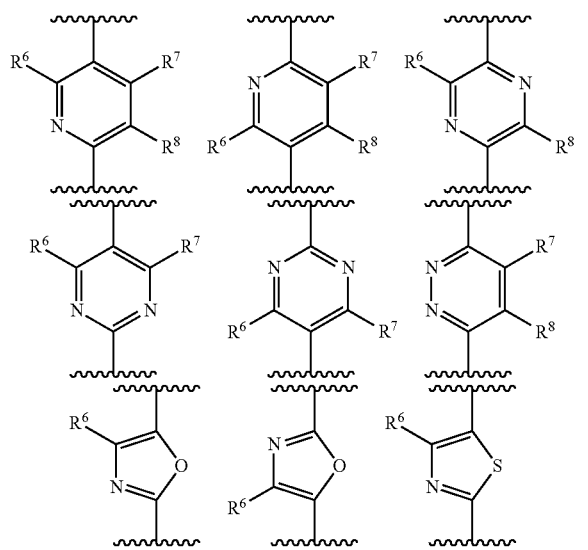

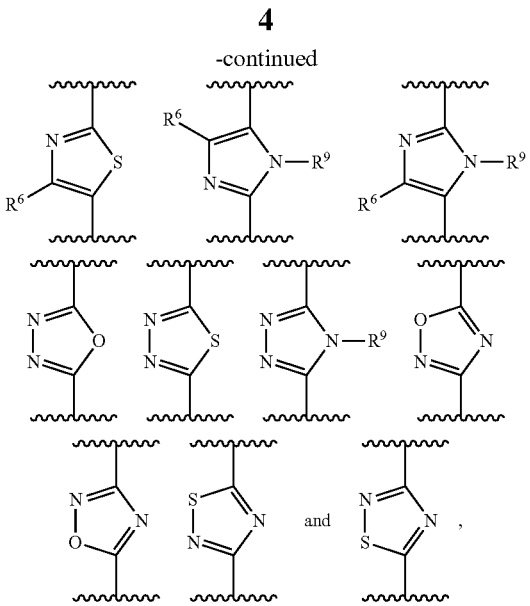

wherein groups $R^6$, $R^7$, $R^8$ and $R^9$ are defined as in general formula 1;

or a salt thereof.

In a further embodiment, the compound is selected from the group consisting of:

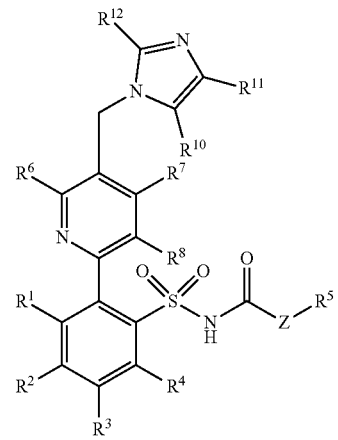

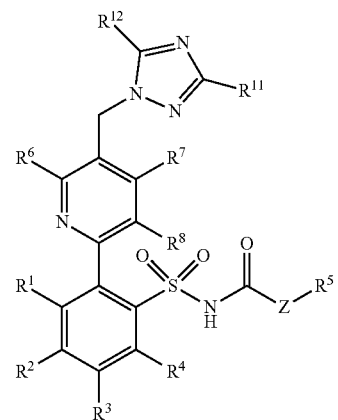

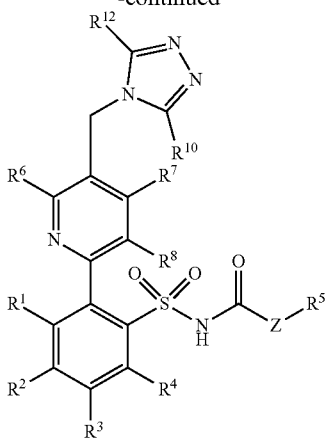
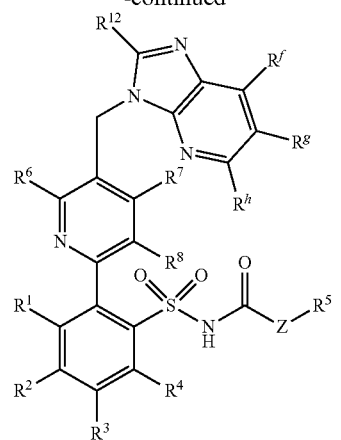
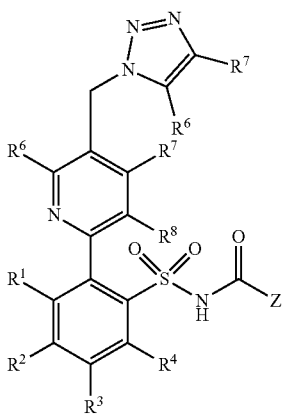
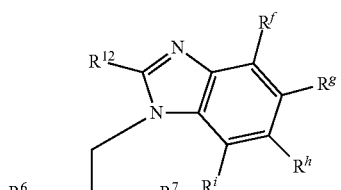
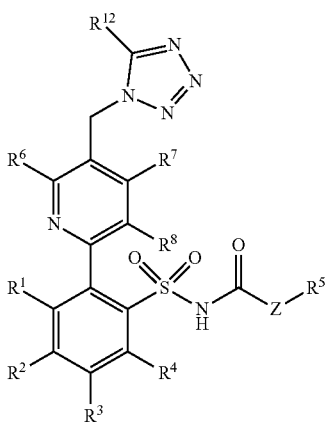
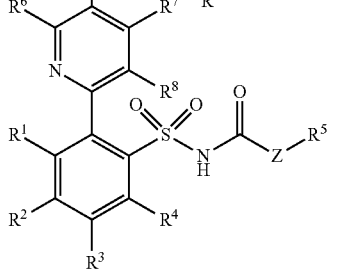
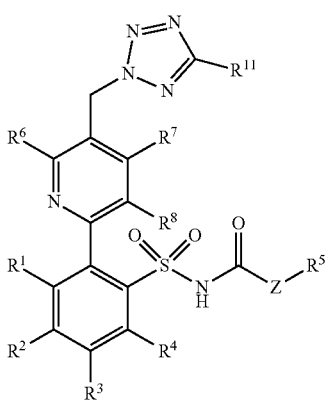
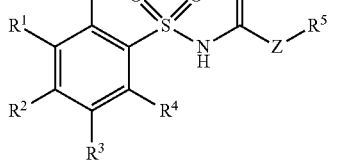

7
-continued
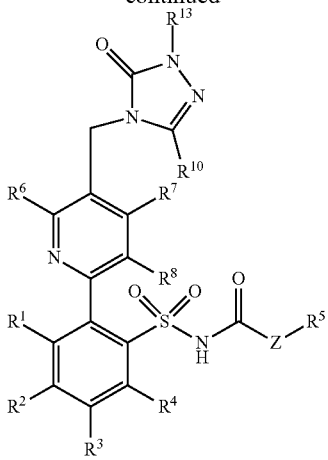
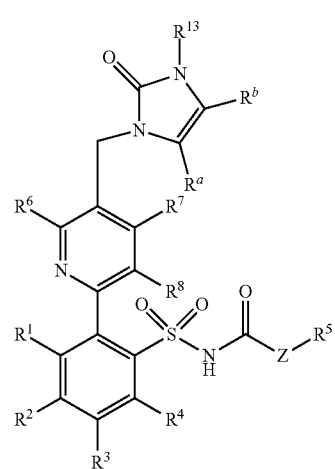
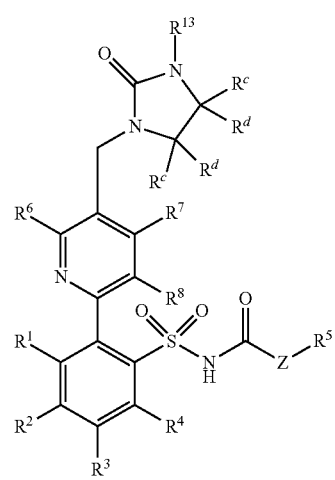
8
-continued
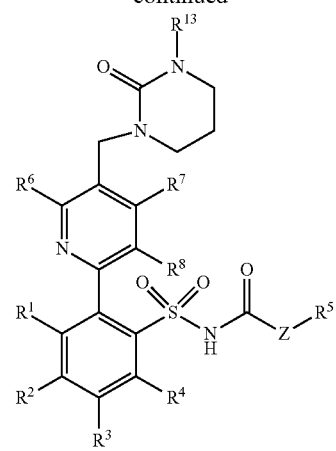
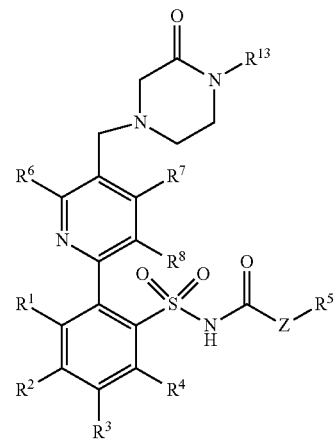
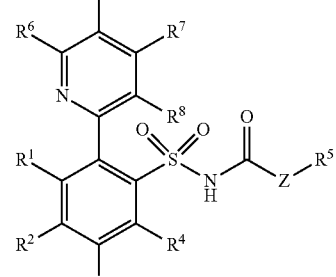
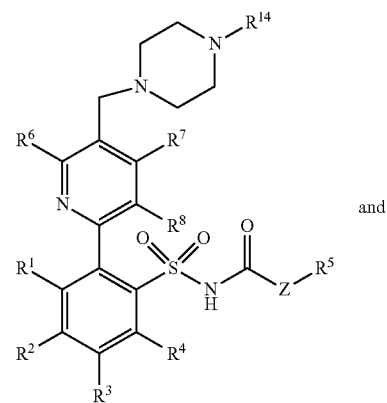
and -continued

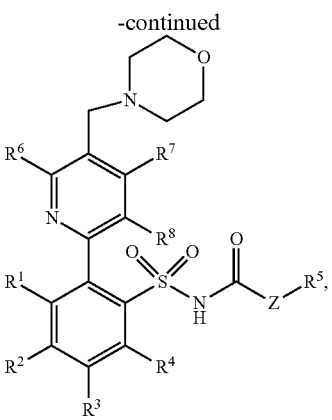

wherein:
R$^1$, R$^2$, R$^3$, R$^4$ R$^5$, R$^6$, R$^7$, R$^8$, R$^9$, R$^a$, R$^b$, R$^d$ and Z are defined as in general formula 1;
R$^{10}$ and R$^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido and carboxy
or R$^{10}$ and R$^{11}$, together with ring A to which they are attached, form a carbocyclic, heterocyclic, aryl or hetoaryl ring;
R$^{12}$ is hydrogen, alkyl, alkenyl, alkynyl, aryl, heteroaryl, halo, hydroxy, hydroxyalkyl, alkoxyalkyl, alkoxy, aryloxy, or acylamido;
R$^{13}$ is hydrogen, alkyl, aryl or heteroaryl;
R$^{14}$ is hydrogen, alkyl, aryl, heteroaryl, acyl, alkoxyacyl, aminoacyl, dialkylaminoacyl, or dialkylaminoacyl; and
R$^f$, R$^g$, R$^h$, and R$^i$, are independently selected from a group consisting of hydrogen, alkyl, alkenyl, alkynyl, aryl, heteroaryl, arylmethyl, heteroarylmethyl, fluoro, chloro, bromo, iodo, hydroxy, amino, alkylamino, alkoxy, aryloxy, alkoxyalkyl, and aryloxyalkyl;
or a salt thereof.

In various further embodiments, R$^2$ is trifluoromethoxy and/or Z is O or —N(H)—. In another embodiment, the compound has the general formula 4a or a salt thereof:

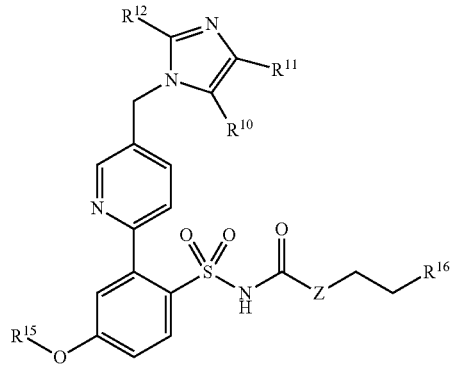

4a wherein:
Z is —O— or —N(H)—;
R$^{10}$ and R$^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido and carboxy,
or R$^{10}$ and R$^{11}$, together with ring A to which they are attached, form a carbocyclic, heterocyclic, aryl or hetoaryl ring;
R$^{12}$ is hydrogen, alkyl, alkenyl, alkynyl, aryl, heteroaryl, halo, hydroxy, hydroxyalkyl, alkoxyalkyl, alkoxy, aryloxy, or acylamido;
R$^{15}$ is alkyl, aryl, heteroaryl, arylmethyl, heteroarylmethyl, trifluoromethyl or pentafluoroethyl; and
R$^{16}$ is hydrogen, hydroxy, methoxy, alkoxy, alkyl, alkenyl, alkynyl, aryl, heteroaryl, amino, alkylamino, or dialkylamino.

In a further embodiment, the compound has the general formula 4a or a salt thereof:

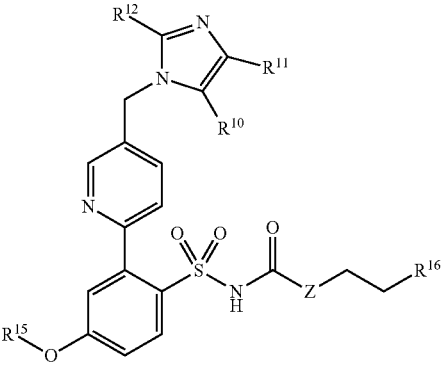

4a wherein:
Z is —O— or —N(H)—;
R$^{10}$, R$^{11}$ and R$^{12}$ are hydrogen;
R$^{15}$ is alkyl, aryl, heteroaryl, arylmethyl, heteroarylmethyl, trifluoromethyl or pentafluoroethyl; and
R$^{16}$ is hydrogen, hydroxy, methoxy, alkoxy, alkyl, alkenyl, alkynyl, aryl, heteroaryl, amino, alkylamino, or dialkylamino.

In another embodiment, the compound has the general formula 4a or a salt thereof:

4a wherein:
Z is —O— or —N(H)—;
R$^{10}$ and R$^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{15}$ is trifluoromethyl and $R^{16}$ is ethyl.

In a further embodiment, the compound has the formula 7

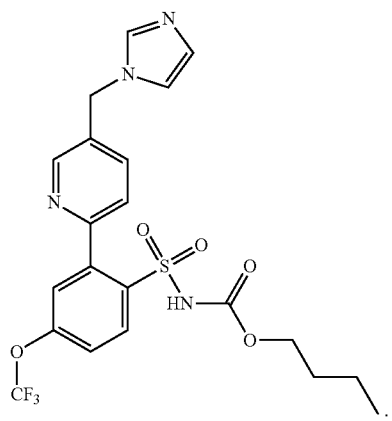

Compound 7

In another aspect, the disclosure provides methods for treating SLE, comprising administering to a subject having SLE an amount effective of a polypeptide comprising angiotensin 1-7 (Asp-Arg-Val-Tyr-Ile-His-Pro) (SEQ ID NO:1) ("A(1-7)"), Nle3 A(1-7) (Asp-Arg-Nle-Tyr-Ile-His-Pro) (SEQ ID NO:2), or a pharmaceutically acceptable salt thereof, to treat the SLE.

DETAILED DESCRIPTION OF THE INVENTION

Figure 1:
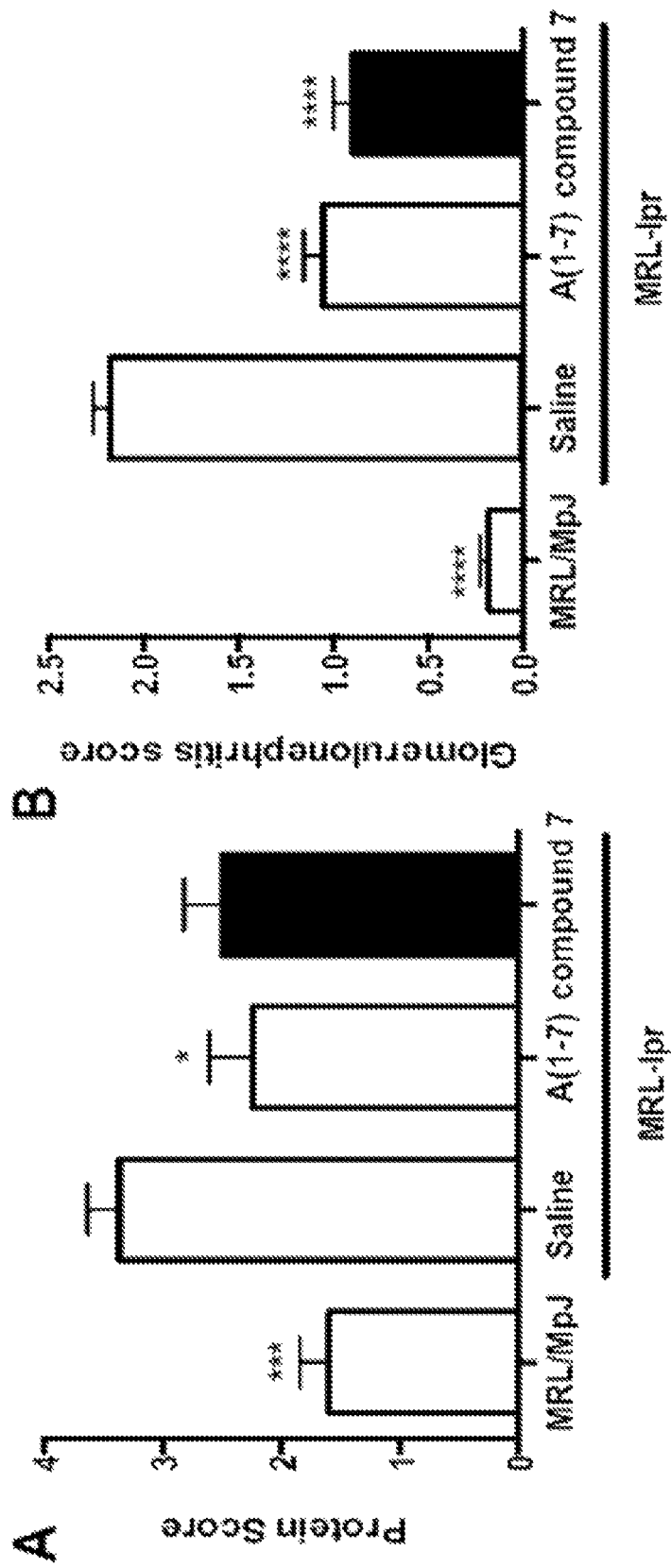
FIG. 1. Treatment with Mas agonists improved kidney health in 14 week old MRL-lpr mice after 6 weeks of treatment. (A) Protein urine concentrations were taken before necropsy and scored according to concentration. (B) Glomeruli were scored from kidney sections stained with H&E. Statistics was done using Prism 6 software t-test and are compared to Saline treated MRL-lpr mice; *$p \leq 0.05$, *$p \leq 0.001$, **$p \leq 0.0001$.

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Indeed, the present invention is in no way limited to the methods and materials described.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

PCT Application PCT/US14/30071 provided novel non-peptidic compounds and compositions (including the synthesis thereof) capable of modulation the Mas receptor of the Renin-Angiotensin System (RAS) and/or capable of mimicking, in part or in entirety, the in vitro and in vivo activities of the endogenous Mas receptor ligand A(1-7), and related peptide Nle3 A(1-7) which has wound healing activity that is blocked by a Mas receptor antagonist.

The present invention describes the use of compounds and compositions for the treatment of systemic lupus erythematosus (SLE).

In one embodiment, this invention provides a method for the treatment of a subject with SLE, comprising the administration to a subject in need thereof an effective amount of a polypeptide comprising or consisting of A(1-7) (Asp-Arg-Val-Tyr-Ile-His-Pro) (SEQ ID NO:1) or Nle3 A(1-7) (Asp-Arg-Nle-Tyr-Ile-His-Pro) (SEQ ID NO:2) to treat the SLE. The polypeptide or salt thereof can further be derivatized to provide enhanced half-life, for example, by linking to polyethylene glycol. The peptide therapeutic or salt thereof may comprise L-amino acids, D-amino acids (which are resistant to L-amino acid-specific proteases in vivo), a combination of D- and L-amino acids, and various "designer" amino acids (e.g., β-methyl amino acids, Ca-methyl amino acids, and Na-methyl amino acids, etc.) to convey special properties.

In another embodiment, this invention provides a method for the treatment of a subject with SLE, comprising the administration to a subject in need thereof an effective amount of a compound having the general formula 1 including salts thereof:

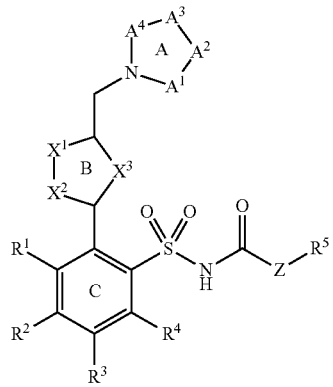

wherein:
ring A is a five-membered or six-membered heteroaryl or heterocyclyl ring containing either a combination of two non-adjacent nitrogen or oxygen atoms, or a combination of three or four nitrogen or oxygen atoms;
ring B is a five-membered or six-membered heteroaryl ring that contains at least one nitrogen atom;
$A^1$, $A^2$, $A^3$, $A^4$ are independently selected from a group consisting of =N—, —C(=O)—, —C($R^a$)=, =C($R^b$)—, —C($R^c$)($R^d$)—N($R^e$)—, —C($R^c$)($R^d$)—O—, and —[C($R^c$)($R^d$)]$_n$—, wherein n is 1 or 2;
$X^1$—$X^2$ is —($R^6$)C—N—, —N—C($R^6$)—, —N—N—, —N—O—, —O—N—, —N—S— or —S—N—;
$X^3$ is —($R^7$)C=C($R^8$)—, —O—, —S—, or —N(R)—;
Z is —O—, —N(H)— or a bond to $R^5$;
$R^a$ and $R^b$ are independently selected from the group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido and carboxy,
or $R^a$ and $R^b$ can also join to form a ring of up to 6 atoms;
$R^c$ and $R^d$ are independently selected from a group consisting of hydrogen, alkyl, aryl, or heteroaryl, provided that $R^c$ and $R^d$, together with the atoms to which they are attached, form a ring of up to 6 atoms;
$R^e$ is hydrogen, alkyl, aryl, heteroaryl, acyl, alkoxyacyl, aminoacyl, dialkylaminoacyl, or dialkylaminoacyl;
$R^1$, $R^3$, $R^4$, $R^6$, $R^7$, and $R^8$ are independently selected from a group consisting of hydrogen, alkyl, alkenyl, alkynyl, aryl, heteroaryl, arylmethyl, heteroarylmethyl, fluoro, chloro, bromo, iodo, cyano, hydroxy, amino, alkylamino, alkoxy, aryloxy, alkoxyalkyl and aryloxyalkyl;
$R^2$ is alkyl, alkenyl, alkynyl, aryl, heteroaryl, arylmethyl, heteroarylmethyl, alkoxy, trifluoromethoxy, perfluoroalkoxy, aryloxy, alkoxyalkyl, or aryloxyalkyl;
$R^5$ is alkyl, aryl, heteroaryl, hydroxyalkyl, carboxyalkyl, alkoxyalkyl, or aryloxyalkyl; and
$R^9$ is hydrogen, alkyl, aryl, heteroaryl, acyl, alkoxyacyl, aminoacyl, dialkylaminoacyl, or dialkylaminoacyl.

In some preferred embodiments, $R^2$ is trifluoromethoxy.
In other preferred embodiments, Z is O or —N(H)—.
In exemplary embodiments, ring A includes but is not limited to a ring selected from a group consisting of:

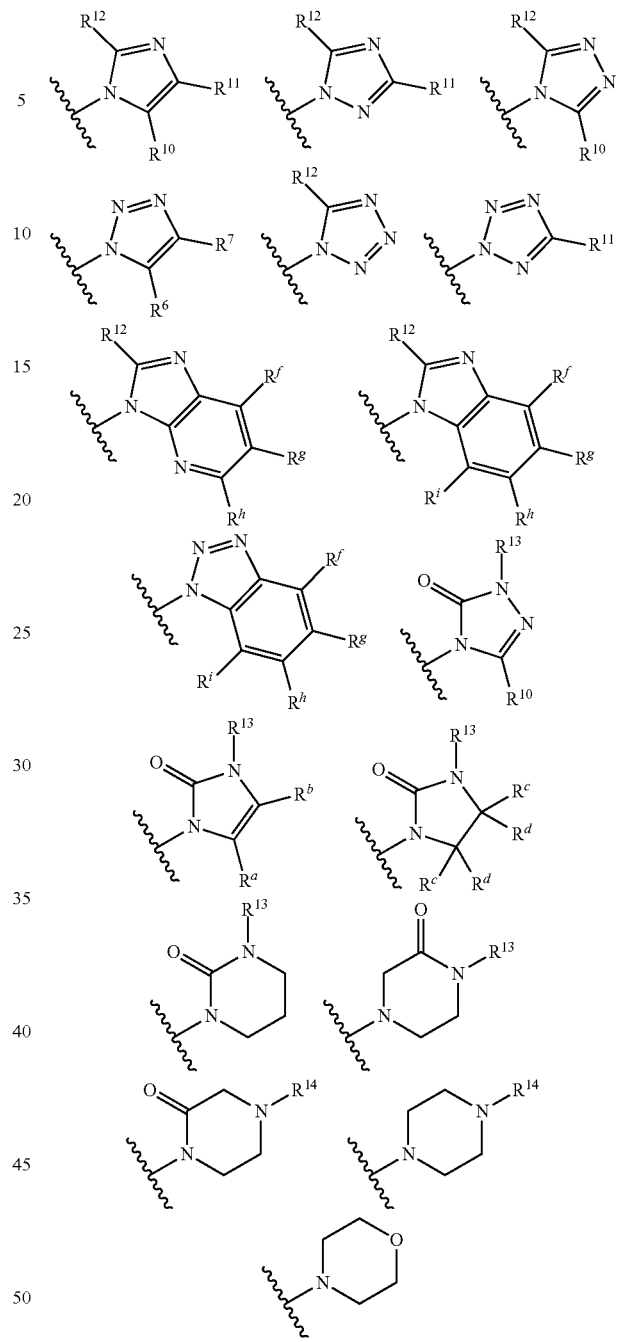

wherein:
$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido and carboxy,
or $R^{10}$ and $R^{11}$, together with ring A to which they are attached, form a carbocyclic, heterocyclic, aryl or hetoaryl ring;
$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;
$R^{13}$ is hydrogen, alkyl, aryl or heteroaryl;

R[14] is hydrogen, alkyl, aryl, heteroaryl, acyl, alkoxyacyl, aminoacyl, dialkylaminoacyl, or dialkylaminoacyl; and R[f], R[g], R[h], and R[i], are independently selected from a group consisting of hydrogen, alkyl, alkenyl, alkynyl, aryl, heteroaryl, arylmethyl, heteroarylmethyl, fluoro, chloro, bromo, iodo, hydroxy, amino, alkylamino, alkoxy, aryloxy, alkoxyalkyl, or aryloxyalkyl;

or a salt thereof.

In other exemplary embodiments, ring B includes but is not limited to a five- or six-membered heteroaryl ring selected from a group consisting of:

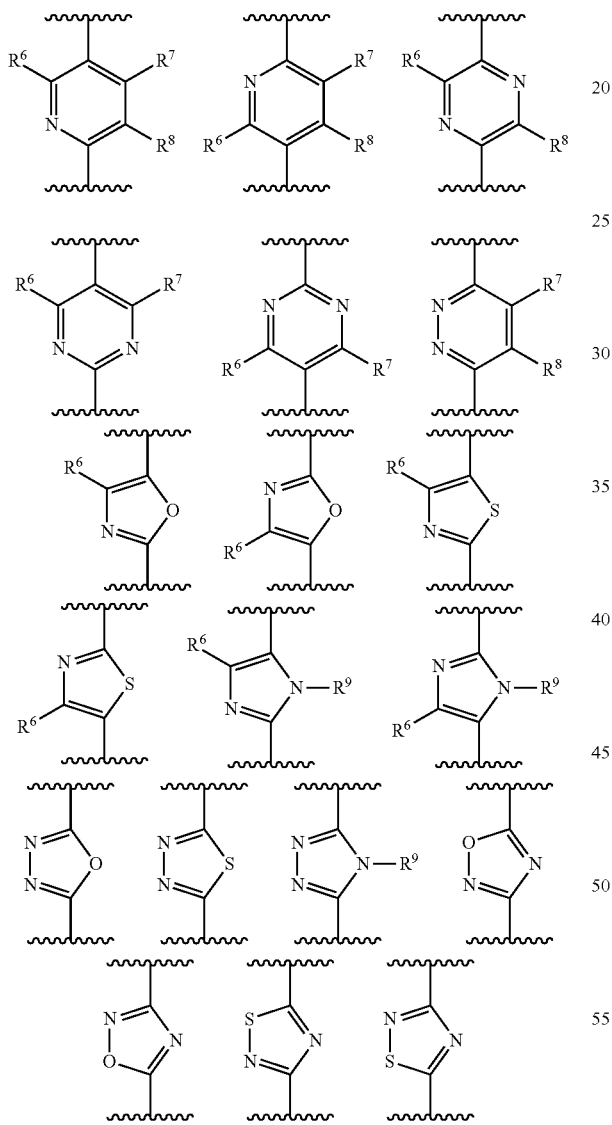

wherein groups R[6], R[7], R[8] and R[9] are defined as in general formula 1

In some exemplary embodiments, the compounds administered in connection with the methods and compositions provided herein have the general formula selected from a group consisting of:

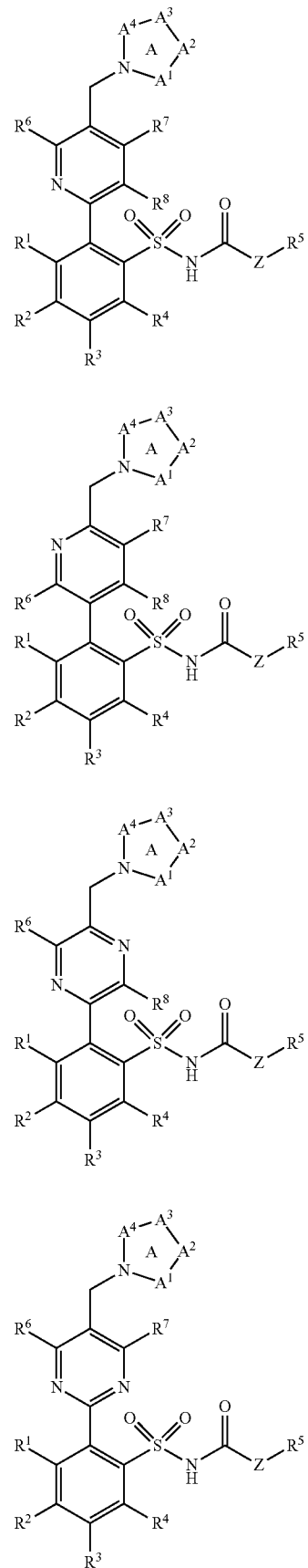

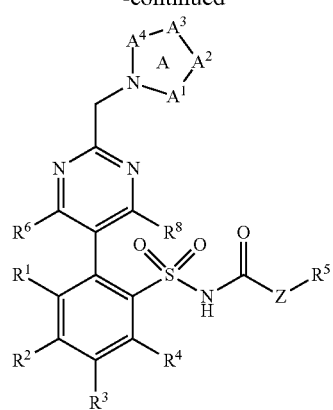
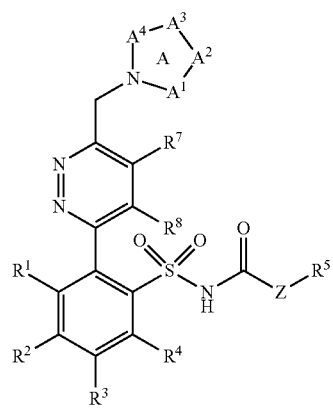
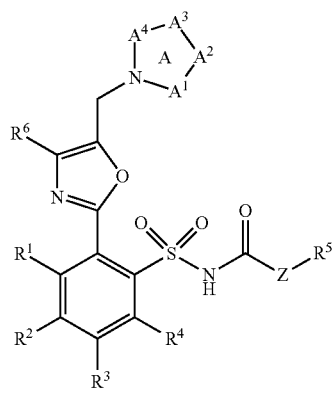
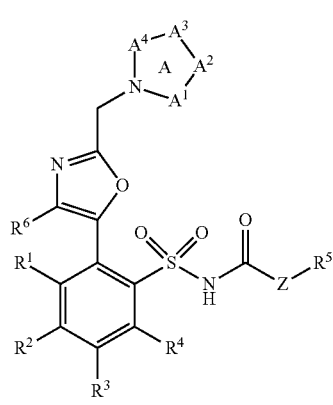
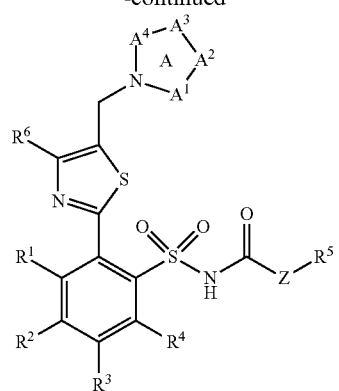
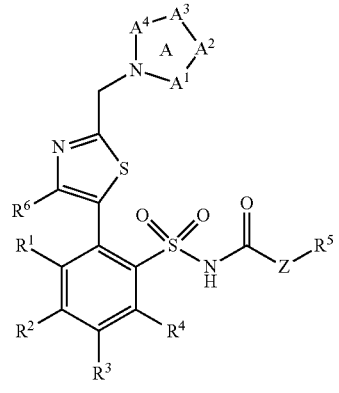
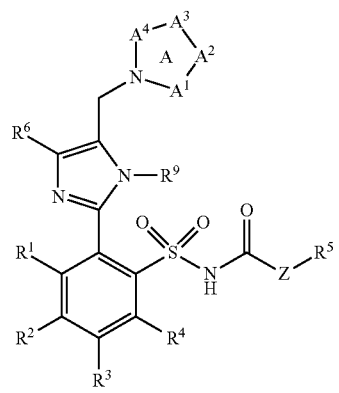
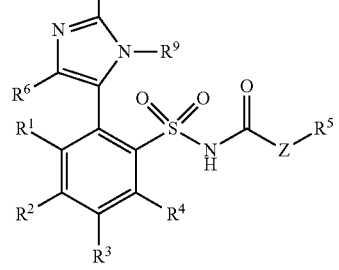

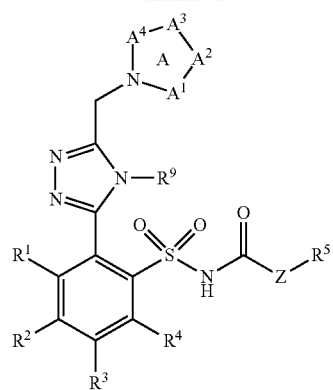
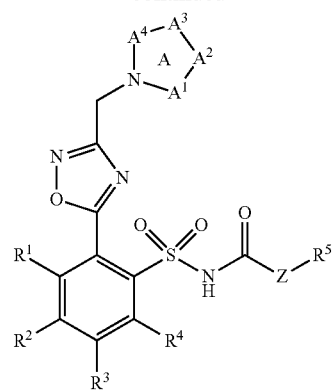
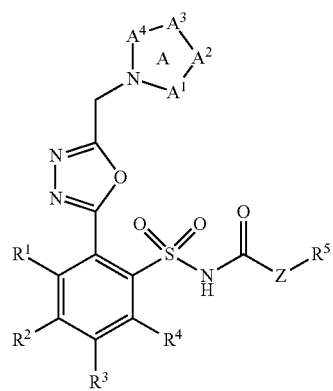
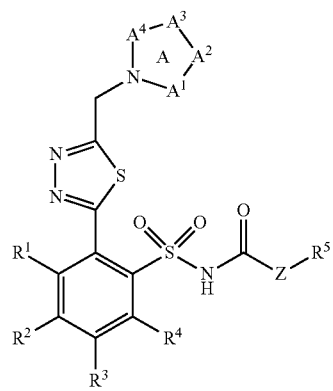
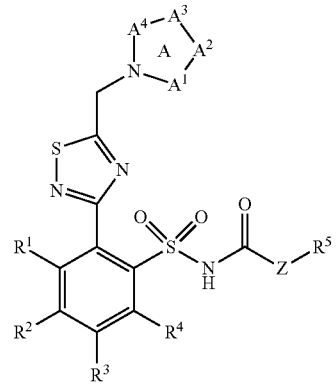
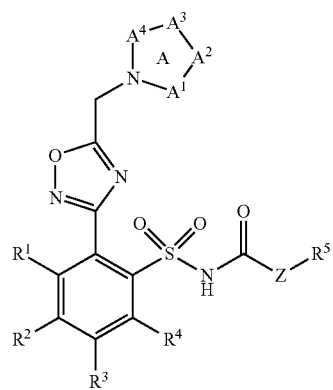
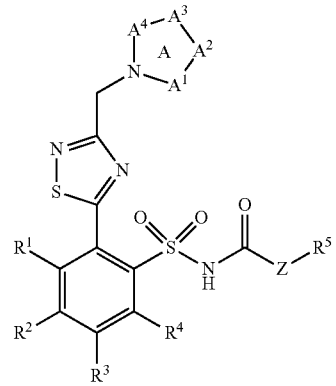
wherein groups $R^1$, $R^2$, $R^3$, $R^4$ $R^5$, $R^6$, $R^7$, $R^8$, $R^9$, $A^1$, $A^2$, $A^3$, $A^4$ and Z are defined as in general formula 1.
In other exemplary embodiments, the compounds have the general formula selected from a group consisting of:

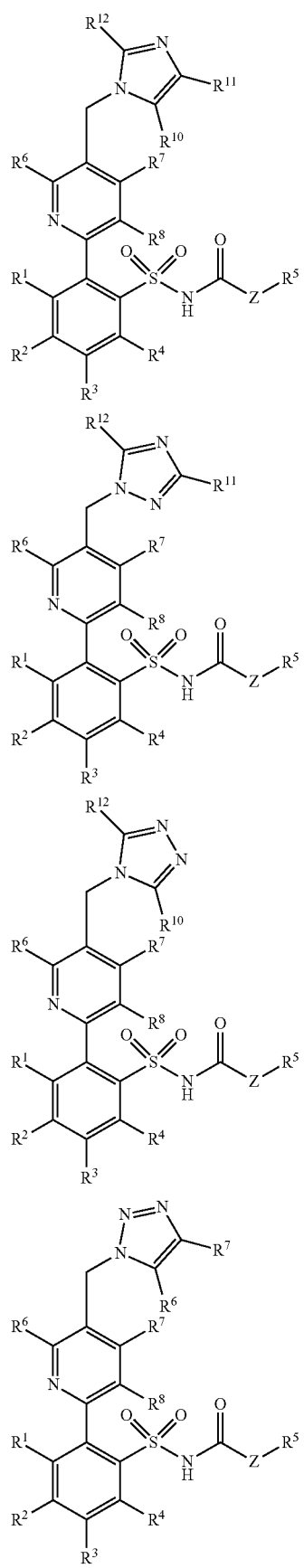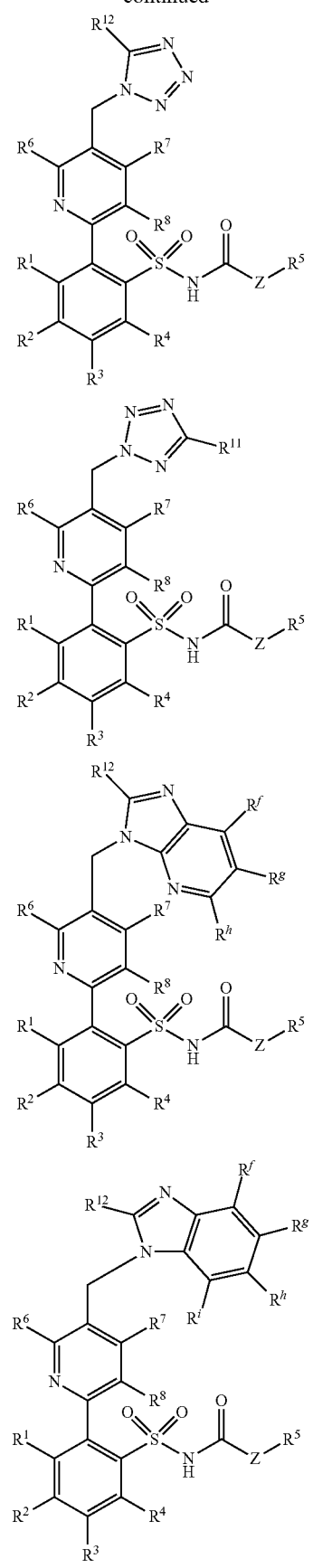

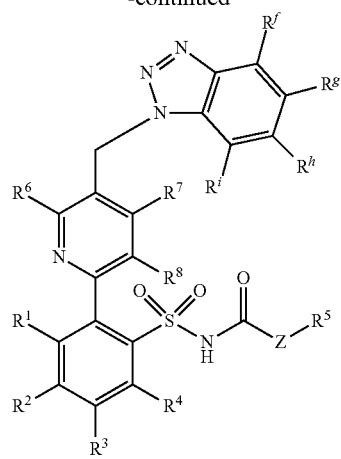
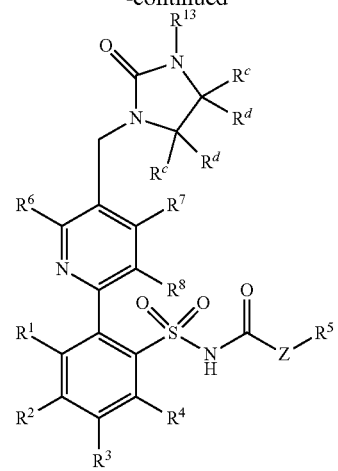
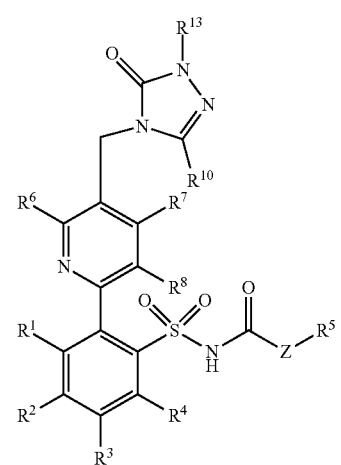
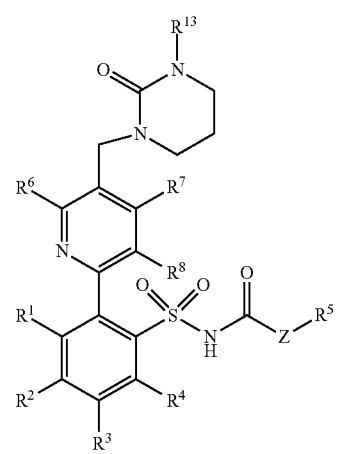
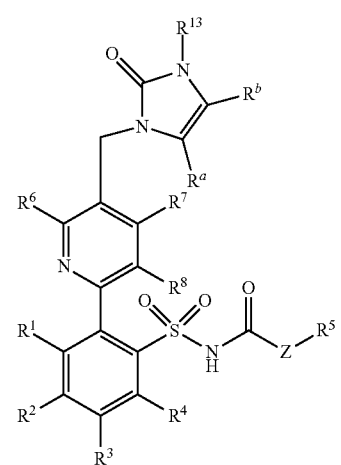
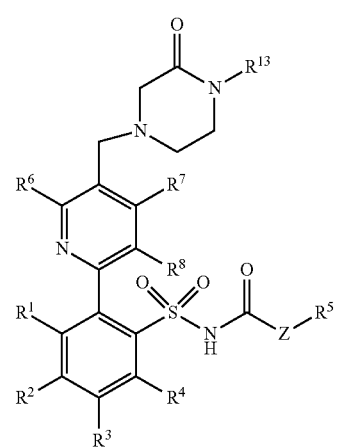

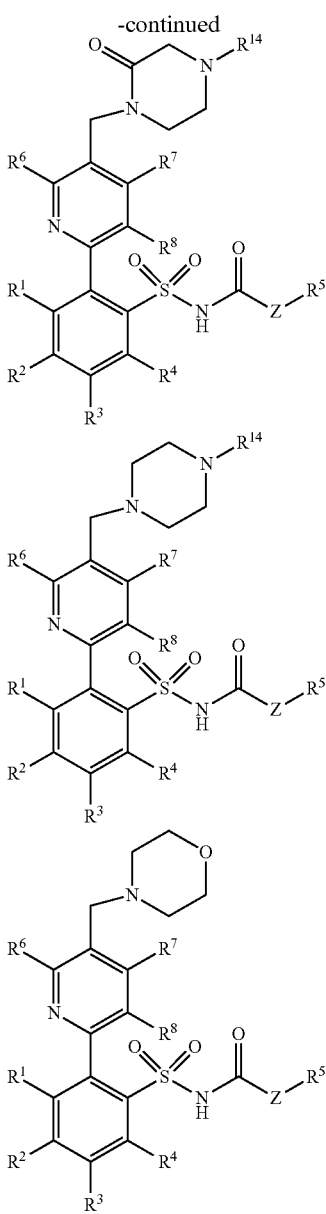

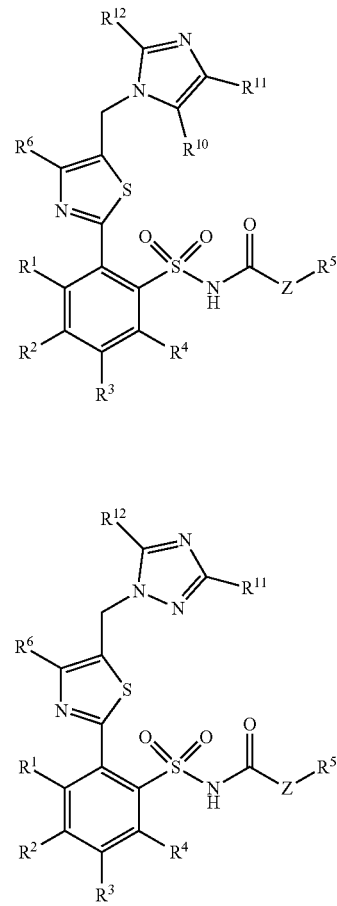

nyl, aryl, heteroaryl, arylmethyl, heteroarylmethyl, fluoro, chloro, bromo, iodo, hydroxy, amino, alkylamino, alkoxy, aryloxy, alkoxyalkyl, and aryloxyalkyl;

or a salt thereof.

In additional exemplary embodiments, the compounds administered in connection with the methods and compositions provided herein have the general formula selected from a group consisting of:

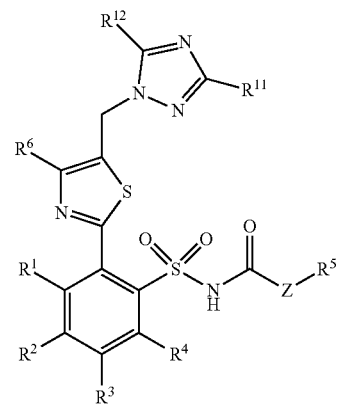

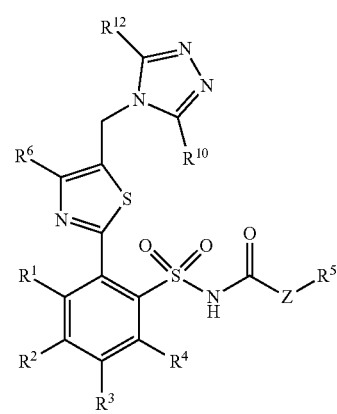

wherein:
R$^1$, R$^2$, R$^3$, R$^4$ R$^5$, R$^6$, R$^7$, R$^8$, R$^9$, R$^a$, R$^b$, R$^c$, R$^d$ and Z are defined as in general formula 1;

R$^{10}$ and R$^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido and carboxy or R$^{10}$ and R$^{11}$, together with ring A to which they are attached, form a carbocyclic, heterocyclic, aryl or hetoaryl ring;

R$^{12}$ is hydrogen, alkyl, alkenyl, alkynyl, aryl, heteroaryl, halo, hydroxy, hydroxyalkyl, alkoxyalkyl, alkoxy, aryloxy, or acylamido;

R$^{13}$ is hydrogen, alkyl, aryl or heteroaryl;

R$^{14}$ is hydrogen, alkyl, aryl, heteroaryl, acyl, alkoxyacyl, aminoacyl, dialkylaminoacyl, or dialkylaminoacyl; and R$^f$, R$^g$, R$^h$, and R$^i$, are independently selected from a group consisting of hydrogen, alkyl, alkenyl, alky- 27
-continued
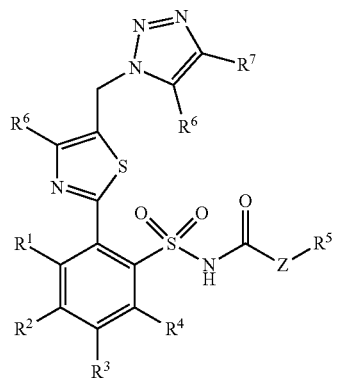
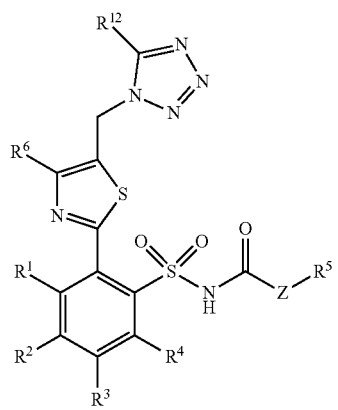
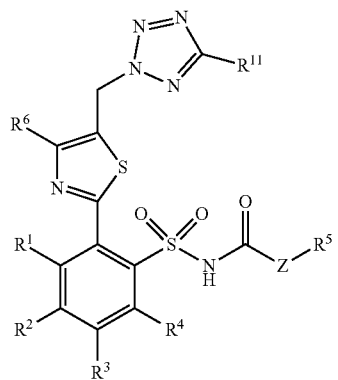
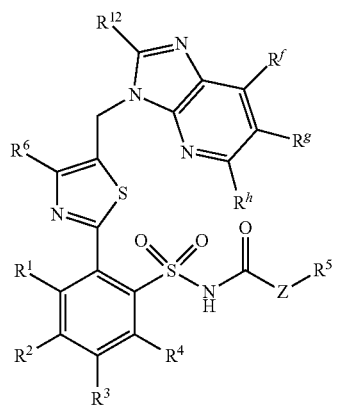
28
-continued
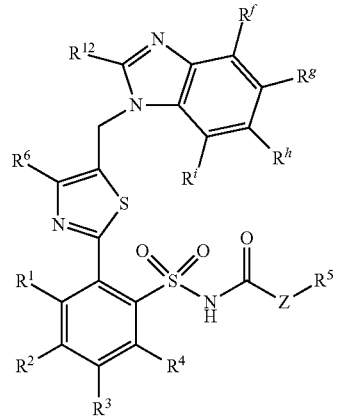
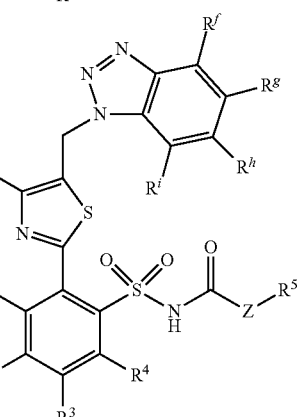
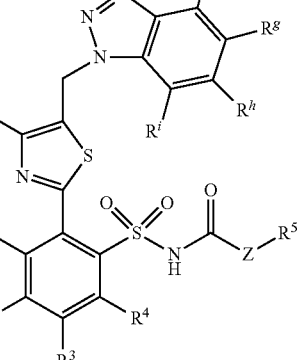
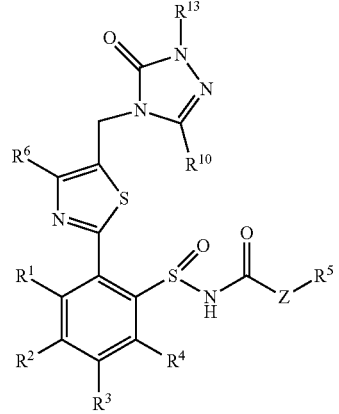
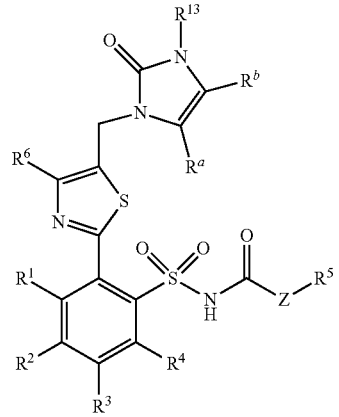

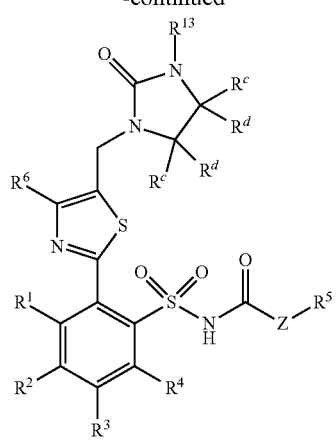

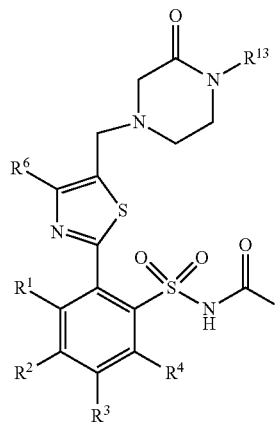

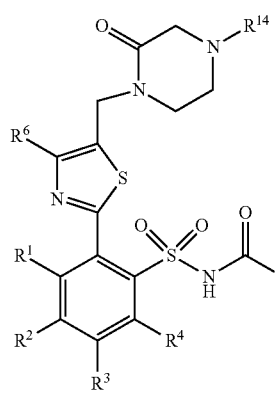

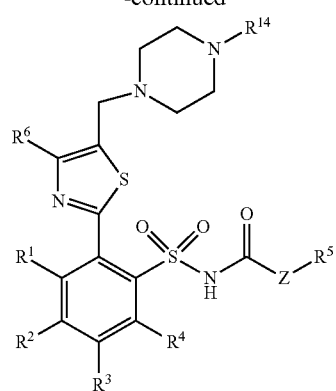

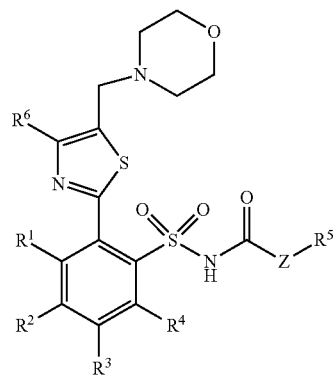

wherein:

$R^1$, $R^2$, $R^3$, $R^4$ $R^5$, $R^6$, $R^7$, $R^8$, $R^9$, $R^a$, $R^b$, $R^c$, $R^d$ and Z are defined as in general formula 1.

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{13}$ is hydrogen, alkyl, aryl or heteroaryl;

$R^{14}$ is hydrogen, alkyl, aryl, heteroaryl, acyl, alkoxyacyl, aminoacyl, dialkylaminoacyl, or dialkylaminoacyl; and $R^f$, $R^g$, $R^h$, and $R^i$, are independently selected from a group consisting of hydrogen, alkyl, alkenyl, alkynyl, aryl, heteroaryl, arylmethyl, heteroarylmethyl, fluoro, chloro, bromo, iodo, hydroxy, amino, alkylamino, alkoxy, aryloxy, alkoxyalkyl, or aryloxyalkyl.

In some preferred embodiments, the compounds administered in connection with the methods provided herein have the general formula 2a,b or 3a,b:

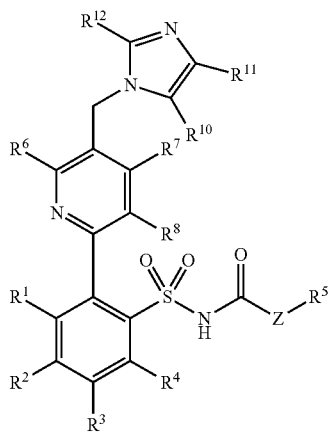

2a

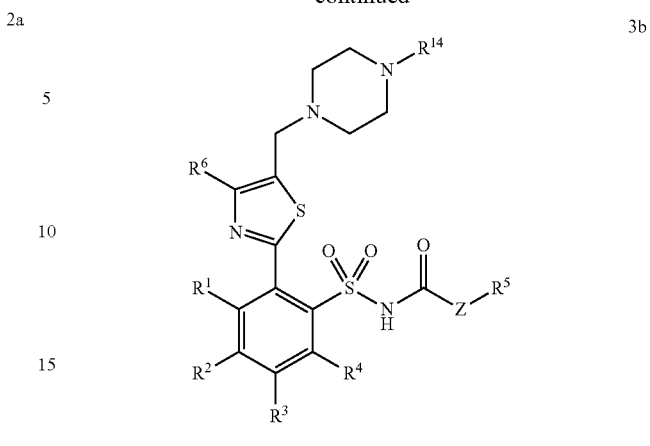

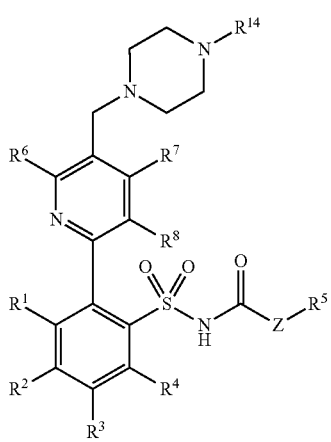

2b

3a

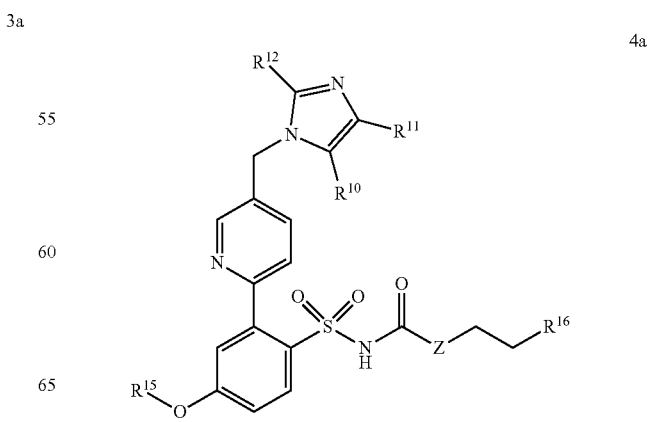

-continued

3b wherein:

R¹, R², R³, R⁴ R⁵, R⁶, R⁷, R⁸, R⁹, Rᵃ, Rᵇ, Rᶜ, Rᵈ and Z are defined as in general formula 1.

R¹⁰ and R¹¹ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that R¹⁰ and R¹¹ can also be joined to form a carbocyclic, heterocyclic, aryl or hetoaryl ring;

R¹² is hydrogen, alkyl, alkenyl, alkynyl, aryl, heteroaryl, halo, hydroxy, hydroxyalkyl, alkoxyalkyl, alkoxy, aryloxy, or acylamido;

R¹³ is hydrogen, alkyl, aryl or heteroaryl;

R¹⁴ is hydrogen, alkyl, aryl, heteroaryl, acyl, alkoxyacyl, aminoacyl, dialkylaminoacyl, or dialkylaminoacyl; and Rᶠ, Rᵍ, Rʰ, and Rⁱ, are independently selected from a group consisting of hydrogen, alkyl, alkenyl, alkynyl, aryl, heteroaryl, arylmethyl, heteroarylmethyl, fluoro, chloro, bromo, iodo, hydroxy, amino, alkylamino, alkoxy, aryloxy, alkoxyalkyl, or aryloxyalkyl.

In further preferred embodiments the compounds administered in connection with the methods and compositions provided herein having the general formula 4a,b, 5a,b or 6a,b:

4a

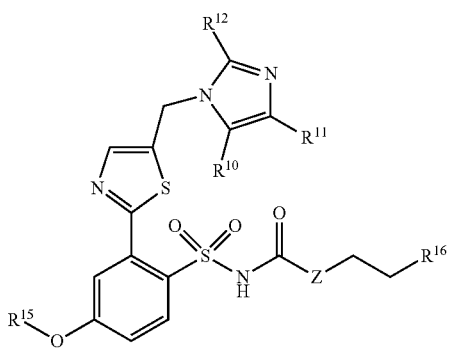
4b

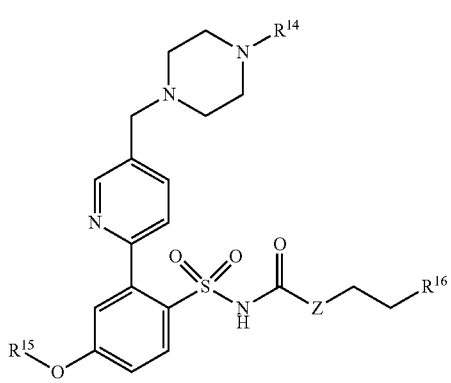
5a

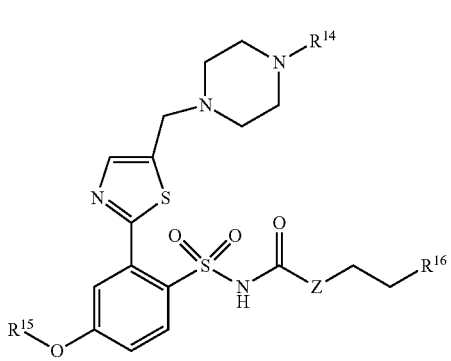
6a

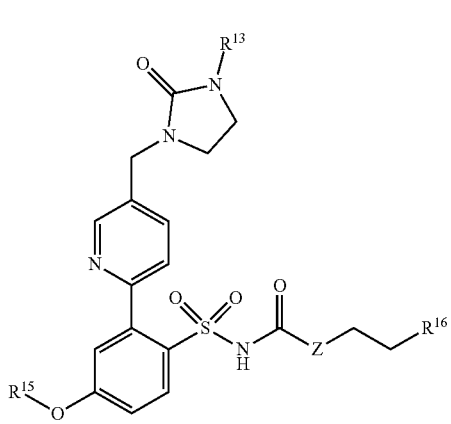
5b

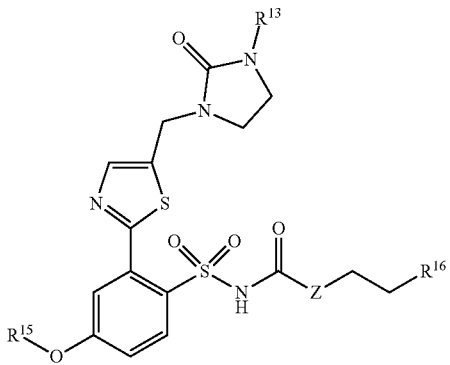
6b wherein:
$R^1$, $R^2$, $R^3$, $R^4$ $R^5$, $R^6$, $R^7$, $R^8$, $R^9$, $R^a$, $R^b$, $R^c$, $R^d$ and Z are defined as in general formula 1.

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{14}$ is hydrogen, alkyl, aryl, heteroaryl, acyl, alkoxyacyl, aminoacyl, dialkylaminoacyl, or dialkylaminoacyl; and $R^{15}$ is alkyl, aryl, heteroaryl, arylmethyl, heteroarylmethyl, trifluoromethyl or pentafluoroethyl; and $R^{16}$ is hydrogen, hydroxy, methoxy, alkoxy, alkyl, alkenyl, alkynyl, aryl, heteroaryl, amino, alkylamino, or dialkylamino.

In some exemplary embodiments, the $R^{10}$, $R^{11}$ and $R^{12}$ are hydrogen, and $R^{14}$ is methyl.

In other exemplary embodiments, $R^{15}$ is trifluoromethyl and $R^{16}$ is ethyl.

Preferred embodiments of the compounds administered in connection with the methods and compositions provided herein have the general formula 4a:

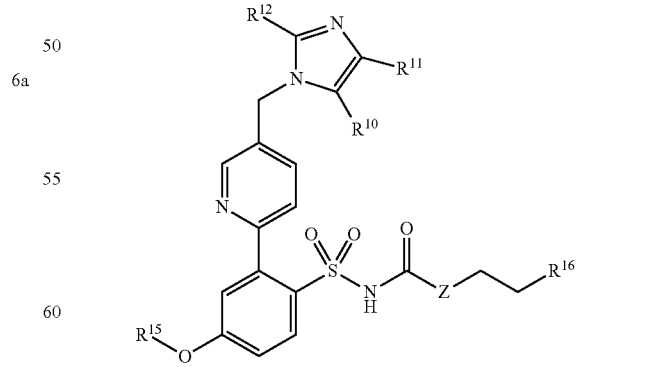
4a wherein:
Z is O or NH
$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{15}$ is alkyl, aryl, heteroaryl, arylmethyl, heteroarylmethyl, trifluoromethyl or pentafluoroethyl; and $R^{16}$ is hydrogen, hydroxy, methoxy, alkoxy, alkyl, alkenyl, alkynyl, aryl, heteroaryl, amino, alkylamino, or dialkylamino.

In some exemplary embodiments, the $R^{10}$, $R^{11}$ and $R^{12}$ are hydrogen.

In exemplary embodiments, $R^{15}$ is trifluoromethyl and $R^{16}$ is ethyl.

Exemplary embodiments of compounds administered in connection with the methods provided herein are provided by compounds 7, 8, 9, 10, and 11:

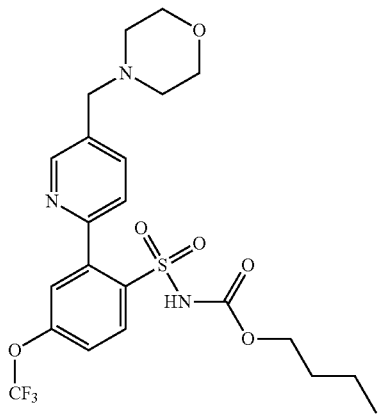
9

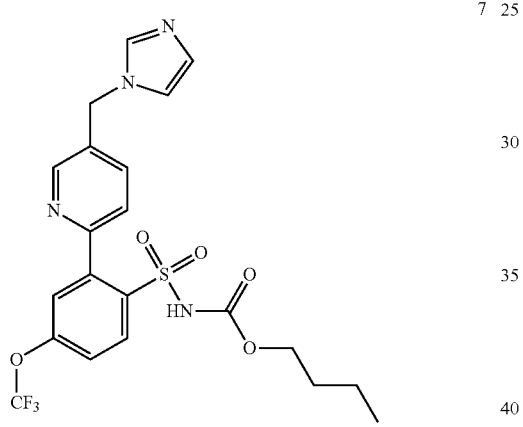
7

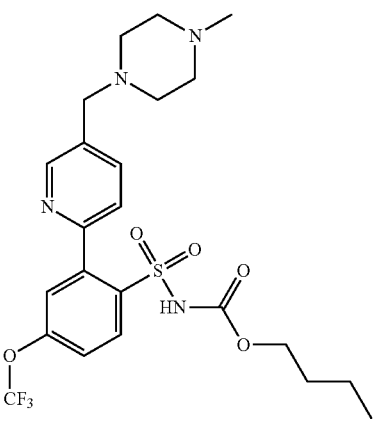
10

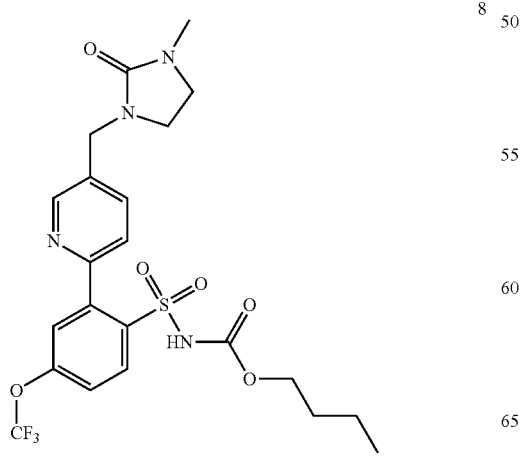
8

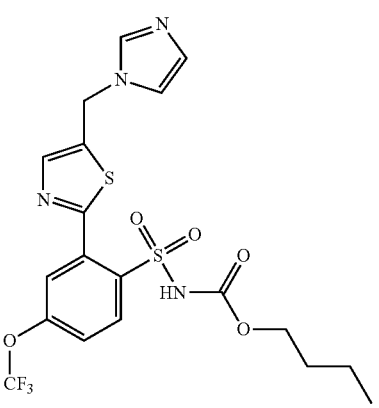
11

A representative exemplary embodiment of the provided methods disclosed herein comprises the administration of Compound 7 for the treatment of SLE:

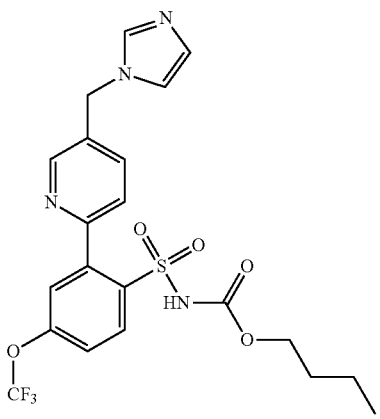

Compound 7

The provided methods are employed in any suitable administrative form, including but not limited to oral, parenteral, or topical administration.

The therapeutic compounds and/or peptides, or pharmaceutically acceptable salts thereof disclosed herein, may be used alone, may be used in combination, or may be used in combination with other therapeutics for treating SLE, including but not limited to belimumab, corticosteroids, and/or hydroxychloroquine. In this embodiment, therapeutic compounds and/or peptides, or pharmaceutically acceptable salts thereof disclosed herein may be administered prior to the other therapeutic(s), concurrently with the other therapeutic(s) (either separately or as a combination), or subsequent to the other therapeutic(s) as deemed appropriate by attending medical personnel. Use of the therapeutic compounds and/or peptides, or pharmaceutically acceptable salts thereof disclosed herein in combination with other standard of care treatments for SLE may permit a significant reduction in dosage of the standard of case treatment, thus significantly reducing side effects.

Amounts effective for treating SLE depend on factors including, but not limited to, the nature of the compound or polypeptide (specific activity, etc.), the route of administration, the stage and severity of the disorder, the weight and general state of health of the subject, and the judgment of the prescribing medical personnel. It will be understood that the amount of the compound, polypeptide, or pharmaceutical composition actually administered will be determined by attending medical personnel, in the light of the above relevant circumstances.

The invention is further described in the attached examples, which are illustrative only, and which are not intended to limit the scope of the invention described in the claims.

Definitions

Unless defined otherwise, all technical and scientific terms used herein have the same meaning as is commonly understood by one of ordinary skill in the art. In the event that there is a plurality of definitions for a term herein, those in this section will control unless stated otherwise.

As used herein, the terms "treatment", "treating", and the like, refer to obtaining a desired pharmacologic and/or physiologic effect. The effect may be therapeutic in terms of a partial or complete cure for a disease and/or adverse symptoms attributable to the disease. "Treatment", as used herein, covers any treatment of SLE, particularly in a human, and includes: (a) limiting development of symptoms or flares from occurring in a subject having SLE; (b) limiting worsening of symptoms or flares in a subject having SLE; (c) inhibiting SLE disease, i.e., arresting SLE development; (d) relieving SLE, i.e., causing regression of SLE. The symptoms of SLE include, but are not limited to, painful and swollen joints, fever, chest pain, hair loss, mouth ulcers, swollen lymph nodes, fatigue, rash (such as malar rash), nephropathy, the presence of antibodies against double and single stranded DNA, and dermal lesions, proteinuria, glomerulonephritis.

The terms "individual," "subject," and "patient," used interchangeably herein, refer to a mammal, including, but not limited to, murines, simians, humans, mammalian farm animals, mammalian sport animals, and mammalian pets. Preferably, the subject herein is human, such as a human female.

As used herein, the nomenclature alkyl, alkoxy, carbonyl, etc. is used as is generally understood by those of skill in the chemical art. As used in this specification, alkyl groups can include straight-chained, branched and cyclic alkyl radicals containing up to about 20 carbons, or 1 to 16 carbons, and are straight or branched. Exemplary alkyl groups herein include, but are not limited to, methyl, ethyl, propyl, isopropyl, isobutyl, n-butyl, sec-butyl, tert-butyl, isopentyl, neopentyl, tert-pentyl and isohexyl. As used herein, lower alkyl refer to carbon chains having from about 1 or about 2 carbons up to about 6 carbons. Suitable alkyl groups may be saturated or unsaturated. Further, an alkyl may also be substituted one or more times on one or more carbons with substituents selected from a group consisting of C1-C15 alkyl, allyl, allenyl, alkenyl, C3-C7 heterocycle, aryl, halo, hydroxy, amino, cyano, oxo, thio, alkoxy, formyl, carboxy, carboxamido, phosphoryl, phosphonate, phosphonamido, sulfonyl, alkylsulfonate, arylsulfonate, and sulfonamide. Additionally, an alkyl group may contain up to 10 heteroatoms, in certain embodiments, 1, 2, 3, 4, 5, 6, 7, 8 or 9 heteroatom substituents. Suitable heteroatoms include nitrogen, oxygen, sulfur and phosphorous.

As used herein, "cycloalkyl" refers to a mono- or multi-cyclic ring system, in certain embodiments of 3 to 10 carbon atoms, in other embodiments of 3 to 6 carbon atoms. The ring systems of the cycloalkyl group may be composed of one ring or two or more rings which may be joined together in a fused, bridged or spiro-connected fashion.

As used herein, "aryl" refers to aromatic monocyclic or multicyclic groups containing from 3 to 16 carbon atoms. As used in this specification, aryl groups are aryl radicals, which may contain up to 10 heteroatoms, in certain embodiments, 1, 2, 3 or 4 heteroatoms. An aryl group may also be optionally substituted one or more times, in certain embodiments, 1 to 3 or 4 times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

As used in this specification, a ring is defined as having up to 20 atoms that may include one or more nitrogen, oxygen, sulfur or phosphorous atoms, provided that the ring can have one or more substituents selected from a group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, phosphonate, phosphonamido, and sulfonyl, and further provided that the ring may also contain one or more fused rings, including carbocyclic, heterocyclic, aryl or heteroaryl rings.

The term "alkenyl" refers to a branched or unbranched hydrocarbon having at least one carbon-carbon double bond.

The term "alkynyl" refers to a branched or unbranched hydrocarbon having at least one carbon-carbon triple bond.

The term "carboxy" refers to a —CO$_2$H group.

The term "hydroxy" refers to an —OH group.

The term "alkoxy" refers to a group of the formula R—O— where R is an "alkyl" as defined herein.

The term "carbocycle" refers to a non-aromatic stable 3- to 8-membered carbon ring which may be saturated, mono-unsaturated or poly-unsaturated.

The term "amino" includes primary, secondary or tertiary amino groups.

The term "cyano" refers to the group —CN.

As used herein, alkenyl and alkynyl carbon chains, if not specified, contain from 2 to 20 carbons, or 2 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds.

As used herein, "heteroaryl" refers to a monocyclic or multicyclic aromatic ring system, in certain embodiments, of about 4 to about 15 members where one or more, in one embodiment 1 to 4, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, triazolyl, tetrazolyl, thienyl, pyridyl, pyrrolyl, N-methylpyrrolyl, quinolinyl and isoquinolinyl.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "halo", "halogen" or "halide" refers to F, Cl, Br or I.

As used herein, "haloalkyl" refers to an alkyl group in which one or more of the hydrogen atoms are replaced by halogen. Such groups include, but are not limited to, chloromethyl and trifluoromethyl.

As used herein, "aryloxy" refers to RO—, in which R is aryl, including lower aryl, such as phenyl.

As used herein, "acyl" refers to a —COR group, including for example alkylcarbonyl, cycloalkylcarbonyl, arylcarbonyl, or heteroarylcarbonyls, all of which may be optionally substituted.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

EXAMPLES

Methods

Protein urine scores. At necropsy a final measurement or proteinuria was done using Urinalysis Reagent Strips (Mountainside Medical Equipment; Marcy, N.Y.). Protein scores signify the level of protein measured in the urine of each mouse and are scored as; 1-15 mg/dl protein, 2-30 mg/dl protein, 3-100 mg/dl protein and 4-300 mg/dl protein.

Glomerulonephritis scores. Twenty glomeruli from kidney sections stained with H&E were scored for each mouse and a mean score was calculated. The glomerulonephritis score was based on a previously published score of 0-4 based on histopathological changes[6]. The scores were defined as: 0, kidney without glomerular lesions; 1, minimal thickening of the mesangium; 2, noticeable increase in both mesangial and glomerular capillary cellularity; 3, preceding conditions, along with superimposed inflammatory exudates and capsular adhesions; 4, obliteration of the glomerular architecture included >70% of glomeruli.

Face rash scores. Mice were monitored daily for skin lesions. Scores of lesions of the face were taken 19, 25, 30, 37 and 40 days after the start of treatment; pictures were taken at different time points throughout the study. Face rash scores were based on location and extent of inflammation and hair loss as follows: 0, no noticeable irritation; 1, little redness, no hair loss or inflammation; 2, minimal rash, little hair loss or inflammation; 3, moderate rash, increased hair loss, light inflammation; 4, pronounced rash, near total hair loss and obvious inflammation; 5, rash is spreading up to the top of the face; 6, obvious wound above nose.

Lymph node weights. At necropsy, inguinal and axillary lymph nodes were dissected and trimmed of any surrounding fatty tissues. They were then weighed using an Adventurer precision balance (Ohaus Corporation, Parsippany, N.J.).

Anti-dsDNA IgG titers. Peripheral blood was collected at necropsy by cardiac puncture with a 1 mL syringe fitted with a 22G needle, transferred into 2 ml K3E K3EDTA VACUETTE® tubes, and stored on ice. The tubes were then spun at 1,500 RPM for 15 min at 4° C. The plasma (top layer) was collected and stored at −20° C. The plasma was then diluted at 1:100 and used in a Mouse Anti-DNA IgG Antibody ELISA Kits (Chondrex Inc, Redmond, Wash.). The average concentration of duplicate samples was calculated against a standard curve and averaged for each mouse.

Results

SLE is an autoimmune disease with an etiology that is diverse and not completely understood. Patients with SLE are usually female (1 male:9 females). SLE is usually diagnosed between the ages of 15 to 44. Although patients are now living longer with available treatments, there is still considerable morbidity and mortality in this population[4]. There is also a considerable economic factor to this disease. On average, patients spend an additional $1,847 to $71,334 US dollars a year on disease related costs, depending on frequency and severity of flare ups[5]. Therapies under development for SLE all rely on broad immunosuppressive protein therapies which are costly, require cumbersome administration, and will likely have many of the same adverse events as existing therapies. Here, we have shown that Mas agonists have potency in one of the most severe models of SLE. These novel therapies also have the potential for oral administration, making them a better therapy for a chronic disease like SLE.

Our study uses the MRL/MpJ-Fas$^{lpr}$/J (MRL-lpr) as a mouse model of SLE and MRL/MpJ mice as controls (control mice do develop SLE but at a much later stage in life). These mice were broken into 4 groups that received once daily subcutaneous injections of treatment starting at 8 weeks of age for 6 weeks: a MRL/MpJ group (n=5) dosed daily with saline, an MRL-lpr group (n=8) dosed with saline, an MRL/MpJ group (n=8) dosed with 0.5 mg/kg of A(1-7), and an MRL/MpJ group (n=8) dosed with 2 mg/kg of Compound 7 (in an aqueous Tween 20 formulation). Throughout the study, the mice were monitored for proteinuria and face lesions. At necropsy, the kidneys and peripheral blood were harvested. The kidneys sections were stained with hematoxylin & eosin (H&E) for evaluation of glomerular health. Blood samples were processed and the plasma was stored at −20° C. for measurement of anti-dsDNA antibodies.

Kidneys are one of the organs most affected by SLE. In this study, we monitored the mice for proteinuria throughout the duration of the study. At the final measurement, MRL-lpr mice treated with saline had significantly higher levels of proteinuria compared to the MRL/MpJ mice that were a lot less advanced in disease state (FIG. 1A). MRL-lpr mice treated with A(1-7) and compound 7 had significantly lower protein scores than those treated with saline. Glomeruli from these mice were scored for pathological abnormalities using kidney sections stained with H&E (FIG. 1B). A glomerulonephritis score revealed that the MRL-lpr mice had significant glomerular pathologies compared to MRL-MpJ mice of the same age. This is consistent with the differences seen in the urine protein score. Both A(1-7) and compound 7 treatment significantly reduced the glomerular pathologies in the MRL-lpr mice, again consistent with trends seen in the urine protein scores. Overall, kidney structure and function are protected by treatment with Mas agonists in this model of SLE.

Figure 2:
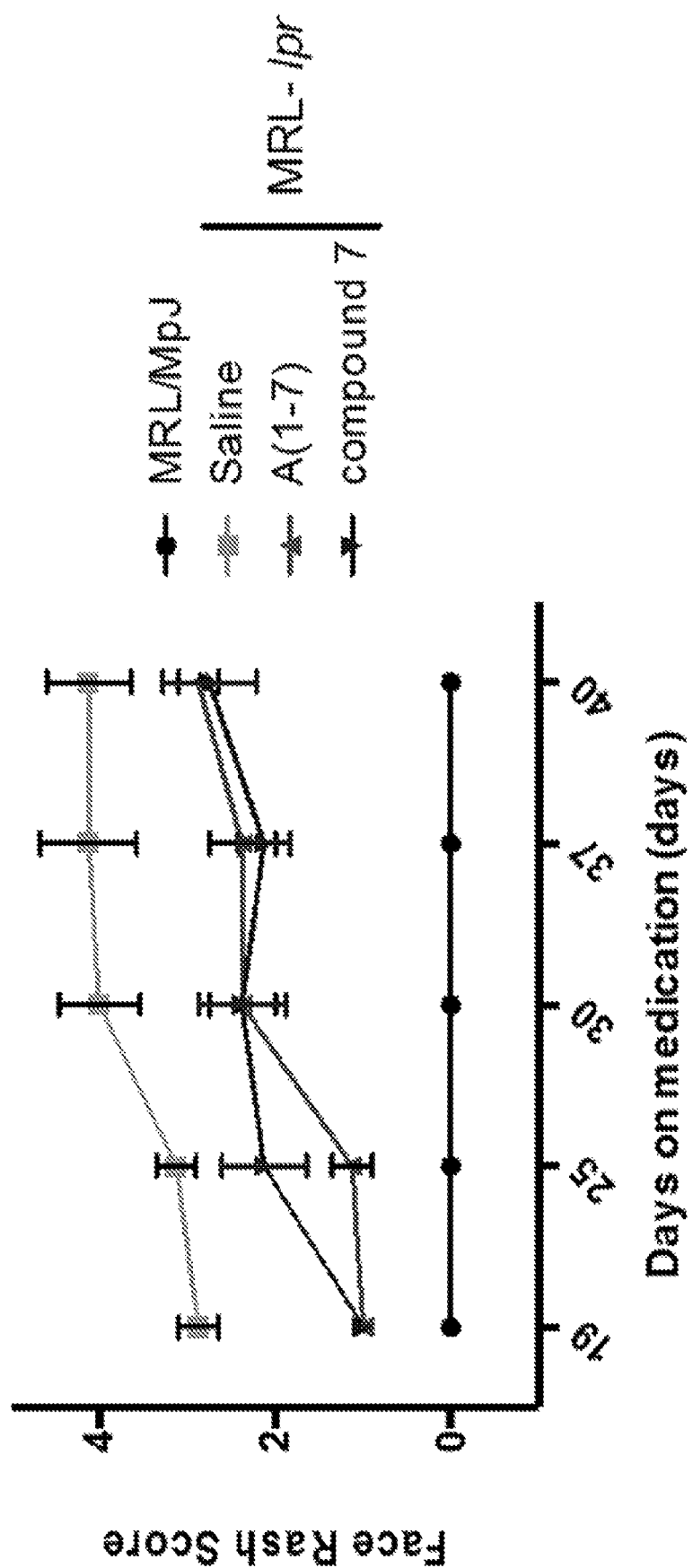
FIG. 2 A(1-7) and compound 7 treatment reduced the severity of the face rashes seen in MRL-lpr mice. Mice were monitored and scored through the study for the appearance of inflammation and hair loss. A(1-7) had a significantly lower score than the saline treated MRL-lrp mice throughout the study. Compound 7 scores were significantly lower only at day 19 and 37. Statistics was done using Prism 6 software t-test, and are compared to Saline treated MRL-lpr mice.

SLE patients also suffer from a malar rash, reddening over the bridge of the nose, during disease flares or after sun exposure that can be painful and can cause scaring. During our study, we monitored the mice for signs of inflammation and/or hair loss anywhere on their face. Mice were scored after 19, 25, 30, 37 and 40 days of treatment. MRL/MpJ mice had no signs of any skin problems at any point during the study. The MRL-lpr mice developed a substantial rash that traveled from their cheeks to the area above the nose and in some cases produced open sores. Mice treated with A(1-7) and compound 7 did have some inflammation and hair loss, but significantly less overall pathologies than the saline treated MRL-lpr mice (FIG. 2). Decrease malar rash is important not only for the quality of life of SLE patients but it may also be indicative of overall reduction in disease pathologies. Here we show another parameter where Mas agonists reduce the severity of symptoms.

Figure 3:
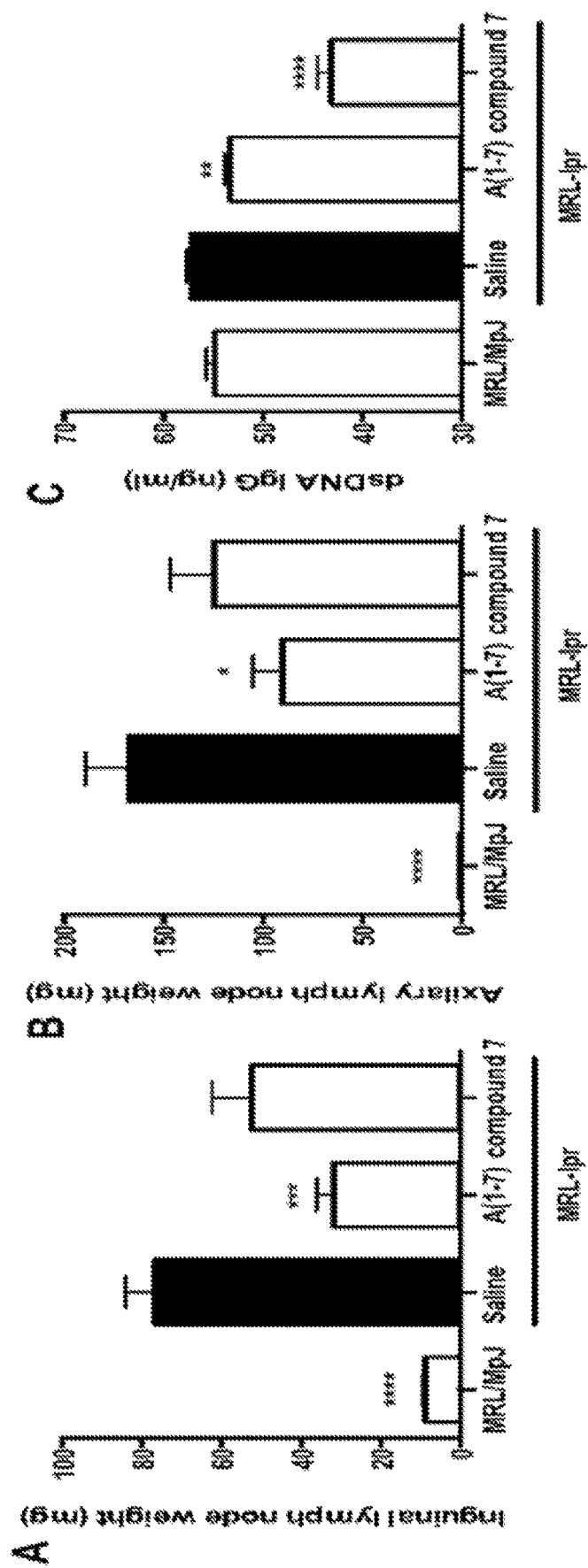
FIG. 3. Mas activation modulates immune parameters important in SLE pathogenesis in 14 week old MRL-lpr mice after 6 weeks of treatment. Inguinal (A) and axilary (B) lymphnodes were dissected and weighed at necropsy. Lymphnodes from MRL-lpr mice treated with A(1-7) were significantly smaller than for those treated with saline. compound 7 treatment also reduced the size but not significantly. Plasma collected at necropsy was used to determine the concentration of circulating anti-dsDNA IgG antibodies in each mouse (C). Both A(1-7) and compound 7 treated mice had significantly lower concentrations of these antibodies compared to the saline treated MRL-lrp mice. Statistics was done using Prism 6 software ANOVA and are compared to Saline treated MRL-lpr mice; *$p \leq 0.05$, $p \leq 0.01$, *$p \leq 0.001$, ****$p \leq 0.0001$. Compound 7=Compound 2.

SLE is a disease of dysfunctional immunity. We looked at 2 different immunological parameters to discern the impact of Mas activation on autoimmune markers of SLE. In this model lymph node size can serve as a surrogate indicator of immune activation, as immune cells are not able to undergo apoptosis after activation and will localize in secondary lymph nodes. In our experiment MRL-lpr mice had significantly larger inguinal and axillary lymph nodes than MRL/MpJ mice (FIGS. 3A & 3B). Treatment with A(1-7) and compound 7 reduced the size of both lymph nodes in MRl-lpr mice. Antibodies against ssDNA and dsDNA are one of the hallmarks of SLE. Immune complexes with these antibodies are thought to be a major reason for the renal pathogenesis seen in these patients. In our study plasma collected from these mice was used to measure the concentration of circulating IgG antibodies against dsDNA (FIG. 3C). In this case MRL/MpJ and MRL-lpr mice had comparable anti-dsDNA IgG levels since they are both used as SLE mouse models. However, both treatment groups (A(1-7) and compound 7) had significantly lower levels of circulating IgG antibodies against dsDNA when compared to the saline treated MRL-lpr mice. It is clear from this evidence that there is reduced pathogenesis in these mice; possibly stemming from immunomodulation.

REFERENCES

1. Uramoto, K. M., Michet, C. J., Jr & Thumboo, J. Trends in the incidence and mortality of systemic lupus erythematosus, 1950-1992. *Arthritis & Rheumatology*. (1999).
2. Aytan, J. & Bukhari, M. Use of biologics in SLE: a review of the evidence from a clinical perspective. *Rheumatology* (2016).
3. Hahn, B. H. Targeted therapies in systemic lupus erythematosus: successes, failures and future. *Annals of the rheumatic diseases* (2011).
4. Fattah, Z. & Isenberg, D. A. Recent developments in the treatment of patients with systemic lupus erythematosus: focusing on biologic therapies. *Expert opinion on biological therapy* (2014).
5. Carter, E. E., Barr, S. G. & Clarke, A. E. The global burden of SLE: prevalence, health disparities and socioeconomic impact. *Nature Reviews Rheumatology* (2016).
6. Wang, B., Yamamoto, Y. & El-Badri, N. S. Effective treatment of autoimmune disease and progressive renal disease by mixed bone-marrow transplantation that establishes a stable mixed chimerism in BXSB 1 recipient mice. *PNAS* (1999).

We claim:

1. A method of treating a subject with systemic lupus erythematosus (SLE) comprising administering to the subject in need thereof an effective amount of a compound having the formula:

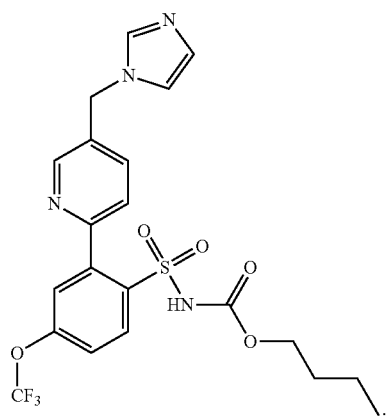 [SMILES: CCCCOC(=O)NS(=O)(=O)c1ccc(OC(F)(F)F)cc1-c1ccc(Cn2ccnc2)cn1]

2. The method of claim 1, wherein the compound is provided as a composition comprising the compound and a pharmaceutically acceptable carrier suitable for oral, parenteral, or topical administration.

3. The method of claim 1, wherein the treating comprises limiting one or more of the following in the subject: lymph node swelling, rash, proteinuria, nephropathy, and antibodies against single and double stranded DNA.

4. The method of claim 1, wherein the subject is a human female.

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Asp Arg Val Tyr Ile His Pro
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Nle

<400> SEQUENCE: 2

Asp Arg Xaa Tyr Ile His Pro
1               5
```

5. The method of claim 1, wherein the compound is administered in combination with one or more of belimumab, a corticosteroid, and/or hydroxychloroquine.

\* \* \* \* \*